United States Patent [19]

Aronson et al.

[11] Patent Number: 4,606,913
[45] Date of Patent: Aug. 19, 1986

[54] HIGH INTERNAL PHASE EMULSIONS

[75] Inventors: Michael P. Aronson, Valley Cottage; Michael F. Petko, Bronx, both of N.Y.

[73] Assignee: Lever Brothers Company, New York, N.Y.

[21] Appl. No.: 103,768

[22] Filed: Dec. 14, 1979

Related U.S. Application Data

[63] Continuation of Ser. No. 945,752, Sep. 25, 1978, abandoned.

[51] Int. Cl.$^4$ .................. A61K 7/021; A61K 7/32; A61K 9/10
[52] U.S. Cl. .................. 424/59; 252/49.5; 252/309; 252/312; 424/DIG. 1; 424/DIG. 4; 424/60; 424/63; 424/65; 424/66; 424/68; 424/70; 514/172; 514/179; 514/182; 514/845; 514/880; 514/881; 514/937
[58] Field of Search .................. 424/59, 171; 252/49.5, 252/312, 309

[56] References Cited

U.S. PATENT DOCUMENTS

| | | | |
|---|---|---|---|
| 2,372,807 | 4/1945 | Brown | 424/365 |
| 2,675,343 | 4/1954 | Clymer et al. | 424/365 |
| 2,742,426 | 4/1956 | Brainerd | 424/365 |
| 3,164,523 | 1/1965 | Fox et al. | 424/195 X |
| 3,448,190 | 6/1969 | Baron et al. | 424/168 X |
| 3,461,073 | 8/1969 | Crowell, Jr. et al. | 424/168 X |
| 3,544,684 | 12/1970 | Scherm | 424/168 X |
| 3,608,073 | 9/1971 | Phares, Jr. et al. | 424/168 |
| 3,816,611 | 6/1974 | Eberhardt et al. | 424/168 |
| 3,932,622 | 1/1976 | Friedman et al. | 424/168 |
| 4,010,254 | 3/1977 | Koulbanis et al. | 424/365 |
| 4,013,786 | 3/1977 | Cella et al. | 424/365 |
| 4,035,513 | 7/1977 | Kumano | 424/168 X |
| 4,104,403 | 8/1978 | Barker et al. | 424/168 |

FOREIGN PATENT DOCUMENTS

211404  7/1957  Australia .................. 424/365

OTHER PUBLICATIONS

Cheesman et al article—Faraday Society, 36, 241 (1940).
Cheesman et al article—*Nature*, 141, 1009 (1938) entitled "An Anomylous Case of Emulsification".
Spalton, Pharmaceutical Emulsion & Emulsifying Agents, 8/1950, pp. 7 to 16, 28 to 44, 26, 20, 46, 52, 53, 66, 67, 84, 85.

*Primary Examiner*—Dale R. Ore
*Attorney, Agent, or Firm*—Milton L. Honig; James J. Farrell

[57] ABSTRACT

An improved high-internal-phase emulsion having increased stability under conditions of long term storage at elevated temperatures and freeze-thaw conditions, methods for preparing and stabilizing said emulsions and cosmetic preparations based thereon are disclosed. The improvement comprises incorporating into said emulsion an amount sufficient to increase the stability of said emulsion of an electrolyte contained in the aqueous phase of the emulsion.

43 Claims, No Drawings

HIGH INTERNAL PHASE EMULSIONS

This is a continuation application of Ser. No. 945,752, filed Sept. 25, 1978, now abandoned.

BACKGROUND OF THE INVENTION

1. Field of the Invention

This invention relates to high-internal-phase emulsions. High internal-phase emulsions, hereafter referred to as HIPE'S, are liquid/liquid immiscible dispersed systems wherein the volume of the internal or dispersed phase occupies a volume more than about 74 to 75 percent of the total volume, i.e. a volume greater than is geometrically possible for close packing of mono-dispersed spheres.

HIPE'S possess radically different properties from emulsions of the low or medium internal phase ratio types. Specifically HIPE'S are non-Newtonian in nature exhibiting a yield valve phenomenon and a decrease in the effective viscosity with shear rate. In contrast to gels which require significant time periods to recover their body when subject to shear HIPE'S, or as they are also known, high internal phase ratio emulsions, recover to high viscosities almost instantaneously. Because of these radically different properties HIPE'S have been subject to investigation with respect to applications in such varied disciplines as: fuels, oil exploration, agricultural sprays, textile printing, foods, household and industrial cleaning, cosmetics, transport of solids, fire extinguishers, and crowd control to name just a few.

HIPE'S appear to have attracted very little interest prior to the mid-nineteen-sixties when workers in the fields of agricultural sprays, low flammability aircraft fuels and textile printing pastes, published papers describing their use properties and preparation. Representative of these early applications and etc. are set forth in the following publications which are incorporated herein by reference:

1. R. E. Ford, C. G. L. Furmidge, J. Colloid & Interface Sci., 22, 331–341 (1966).
2. R. E. Ford, C. G. L. Furmidge, J. Sci. Food Agric., 18 (9), 419-28 (1967).
3. J. P. Colthurst, C. G. L. Furmidge, R. E. Ford, J. A. Pearson. The Formulation of Pesticides. S. C. I. Monograph No. 21 (1966).
4. J. Nixon, A. Beerbower, Am Chem. Soc. Petrochem. Preprints 14, 49–59 (1969).
5. A. Beerbower, J. Nixon, Am. Chem. Soc. Petrochem. Preprints 14, 62–71 (1969).
6. A. Beerbower, J. Nixon, W. Philippoff, T. J. Wallace, S. A. E. Transactions, Section 2, 1446-54 (1968).
7. A. Beerbower, J. Nixon, T. J. Wallace, J. Aircraft, 5 (4), 367–72 (1968).
8. J. Nixon, A. Beerbower, T. J. Wallace, Mech. Eng., 90 27–33 (1968).
9. I. Rusgnak, L. G. Bercsenyi, Magy. Kem. Labja., 25 (9), 452–7 (1970).
10. L. G. Berscenyi, Textilveredlung, 7 (12) 778–780 (1972).
11. L. G. Berscenyi, M. I. Khalil, A. Kantouch, A. Hebeish, Kolor. Ertesito, 15, 254–260 (1973).
12. L. G. Berscenyi, A. Hebeish, A. Kantouch, M. I. Khalil, Kolor. Ertesito, 16, 73–81 (1974).
13. A. Kantouch, M. I. Khalil, L. G. Berscenyi, A. Hebeish, Kolor, Ertesito, 16, 140–147 (1974).

Recognized, perhaps, as one of the foremost workers in the areas of HIPE'S is K. J. Lissant of the Petrolite Corporation, St. Louis, Mo., who has published numerous papers in the field and who holds numerous patents related to HIPE technology. These publications and patents include the following which are incorporated herein by reference:

1. K. J. Lissant, J. Colloid & Interface Sci., 22, 462–468 (1966).
2. K. J. Lissant, J. Soc. Cosmetic Chem., 21, 141–154 (1970).
3. K. J. Lissant, K. G. Mayhan, J. Colloid & Interface Sci., 42, 201–207 (1973).
4. K. J. Lissant, Emulsions and Emulsion Technology. Part 1 (Dekka), 49–66 (1974).
5. K. J. Lissant, B. W. Peace, S. H. Wu, K. G. Mayhan, J. Colloid & Interface Sci., 47, 416–423 (1974).
6. K. J. Lissant, Colloid & Interface Sci., Proceedings of 50th Int. Conf., 4 473–485 (1976).
7. K. J. Lissant (Petrolite Corp.), U.S. Pat. No. 3,343,599, Sept. 26, 1967.
8. K. J. Lissant (Petrolite Corp.), U.S. Pat. No. 3,352,109, Nov. 14, 1967.
9. K. J. Lissant (Petrolite Corp.), U.S. Pat. No. 3,396,537, Aug. 13, 1968.
10. K. J. Lissant (Petrolite Corp.), U.S. Pat. No. 3,490,237, Jan. 20, 1970.
11. K. J. Lissant (Petrolite Corp.), U.S. Pat. No. 3,523,826, Aug. 11, 1970.
12. K. J. Lissant (Petrolite Corp.), U.S. Pat. No. 3,539,406, Nov. 10, 1970.
13. K. J. Lissant (Petrolite Corp.), U.S. Pat. No. 3,565,817, Feb. 23, 1971.
14. K. J. Lissant (Petrolite Corp.) U.S. Pat. No. 3,613,372, Oct. 19, 1971.
15. K. J. Lissant (Petrolite Corps.), U.S. Pat. No. 3,617,095, Nov. 2, 1971.
16. K. J. Lissant (Petrolite Corp.), U.S. Pat. No. 3,700,594, Oct. 24, 1972.
17. K. J. Lissant (Petrolite Corp.), U.S. Pat. No. 3,732,166, May 8, 1973.
18. K. J. Lissant (Petrolite Corp.), U.S. Pat. No. 3,974,116. Aug. 10, 1976.
19. K. J. Lissant (Petrolite Corp.), U.S. Pat. No. 3,983,213, Sept. 28, 1976.
20. K. J. Lissant (Petrolite Corp.), U.S. Pat. No. 3,988,508, Oct. 26, 1976.
21. K. J. Lissant (Petrolite Corp.), G. B. Pat. No. 1227 345, Apr. 7, 1971.
22. K. J. Lissant (Petrolite Corp.), G. B. Pat. No. 1227 346, Apr. 7, 1971.
23. K. J. Lissant (Petrolite Corp.), G. B. Pat. No. 1465 528, Feb. 23, 1977.
24. K. J. Lissant (Petrolite Corp.) G. B. Pat. No. 146 529, Feb. 23, 1977.
25. K. J. Lissant (Petrolite Corp.), G. B. Pat. No. 146 530, Feb. 23, 1977.
26. K. J. Lissant (Petrolite Corp.), Ger. Offen. 2408663, Aug. 7, 1975.

As stated, this invention relates to high-internal-phase emulsions. More particularly, the invention relates to HIPE'S wherein the liquid/liquid immiscible dispersed systems are water and oil, i.e. having an aqueous phase and an oil phase. By oil phase is meant a material, solid or liquid, but preferably liquid at room temperature that broadly meets the following requirements:

1. is only sparingly soluble in water;
2. has a low surface tension; and 3. possesses a characteristic of a greasy feel to the touch.

Materials included under this definition include, for example, but in no way limited to: straight, branched or cyclic parafin compounds, vegetable oils, esters of fatty acids, or alcohols and silicon oils.

Both oil-in-water, hereafter referred to as o/w, and water-in-oil, hereafter referred to as w/o, HIPE'S are subject to the instant invention. By oil-in-water is meant that the oil phase is dispersed in the water phase and conversely, by water-in-oil is meant that the water phase is dispersed in the oil phase.

While HIPE'S are defined as emulsions whose internal phase comprises more than about 74 to 75 of the emulsion by volume, usually, the volume fraction of the internal phase in such emulsions is greater than 90 percent and frequently is about 95 percent with some being reported as high as 98 percent.

Both o/w and w/o HIPE's have several properties which make them potentially useful in a variety of applications. These emulsions are viscous fluids and have appreciable yield values. Because of their high viscosity and lower flammability compared to the separate internal oil phase, these emulsions have been proposed as rocket and jet fuels. Water-in-oil emulsions which are 90–96 percent aqueous phase can be prepared in forms ranging from a pourable fluid to a stiff gel. These emulsions can find application in several areas such as:

1. in cosmetics and drugs as an inexpensive vehicle or suspending medium for other ingredients such as sunscreens, emollients, humectants, etc,;
2. in foods such as in dietary products, dressings, and sauces.

Although these emulsions are attractive in terms of cost versus performance (since they are mainly water), the problem until now, has concerned the type of emulsifier required to produce emulsions of adequate stability.

Because HIPE'S are so concentrated, there is great stress applied to the films separating the water droplets in the emulsion. Such stress is quite demanding on the emulsifier and up until now, rather unique and in many cases, rather complicated or sophisticated and expensive emulsifiers were required to obtain reasonably stable HIPE'S. Such emulsifiers have not been readily available and must be specially synthesized. Moreover, since it is generally recognized that an emulsifier which works well with one emulsion composition may not work well with another emulsion composition, the synthesis of a wide range of expensive exotic emulsifiers is currently required in order to stabilize the various types of compositions for which one may to employ HIPE'S.

THE STATE OF THE ART

As stated previously, previous work on stabilizing emulsions has been confined to rather complicated emulsifiers.

The instant invention is directed to an improved high-internal-phase emulsion of the type comprising an aqueous phase, an oil phase, and an emulsifier. The improvement comprises incorporating into said emulsion an amount sufficient to increase the stability of said emulsion of an electrolyte contained in said aqueous phase.

The relationship between electrolyte and emulsions of the low and medium internal phase types is well known, and it is generally recognized that electrolytes are incompatible with emulsions generally causing the dispersed and continuous phases to separate into distinct liquids. In fact, a significant amount of work has been done to devise systems that will allow the incorporation of electrolytic materials so that the specific property of the electrolyte may be employed.

In Brown, U.S. Pat. No. 2,322,822 an emulsion comprising an oil phase, a water phase and an electrolyte is disclosed as being stabilized by the inclusion of an emulsifier consisting of a mixture of hexide mono ester of a fatty acid having at least six carbon atoms and the other esters produced in the reaction of a polyhydroxylic material selected from the group consisting of hexitols, hexitans, hexides, and the said fatty acid with at least six carbon atoms, said mixture having a ratio of fatty acid equivalents to carbon atoms of polyhydroxylic residue of about 0.15 to 0.25 and the ratio of hydroxyl value to ester value of said mixture being about 0.5 to 2.0. As can be seen, the stabilization of an emulsion, which without the inclusion of an electrolyte could have been accomplished simply, when containing an electrolyte, required a specific and complex emulsifier system.

In Foley, et al., U.S. Pat. No. 3,244,638 there is disclosed an emulsion composition of the water-in-oil type which is claimed to remain stable at high temperatures and in the presence of electrolytes. The key to the stability is stated to be the emulsifier composition which consists of:

1. about 1 to about 5 parts by weight of the condensation product of an amine, selected from the group consisting of mono-and dialkyl, mono-and dialkanol amines, said alkyl and alkanol amines having from 1 to 8 carbon atoms in the alkyl and alkanol chains, alkyl polyamines selected from the group consisting of ethylene diamine, diethylene triamine, triethylene tetramine and tetraethylene pentamine, and mixtures thereof, with about an equal molar amount of a fatty acid chosen from the group consisting of aliphatic monocarboxylic acids having from 8 to 22 carbon atoms in the aliphatic chain and reactive esters and halides thereof;
2. about ⅛ to about 2 parts by weight of a long chain aliphatic monohydric alcohol having from 8 to 22 carbon atoms in the aliphatic chain; and
3. about 0 to about 5 parts by weight of a coupling agent selected from the group consisting of aliphatic monohydric alcohols having from about 3 to about 5 carbon atoms in the aliphatic chain, water immiscible liquid chlorinated hydrocarbons, and low boiling liquid aliphatic and aromatic hydrocarbons having fat solubilizing properties and mixtures thereof. Again as can be seen, the destabilizing action of the electrolyte required a specific and complex emulsifier system.

In Lissant, U.S. Pat. No. 3,352,109 there is disclosed the use of HIPE'S in rocket and jet fuels having the characteristics of both liquid and solid fuels.

In Lissant, U.S. Pat. No. 3,892,881 there is disclosed non-Newtonian cosmetic, nutritive and pharmaceutical compositions using HIPE'S.

In Lissant, U.S. Pat. No. 3,490,237 there is disclosed a thixotropic hydrocarbon-in-water emulsion fuel.

In Lissant, U.S. Pat. No. 3,396,537 there is disclosed emulsions of hydrazine and hydrazine derivative useful for rocket fuel.

In each of the above cases specific, complicated emulsion systems must be employed and in many cases be specifically tailored for their particular use.

Thus, while the art of HIPE'S has developed along the direction of various applications of the emulsions to different disciplines wherein their radical properties may be employed the stabilization of such emulsions still requires the use of specific sophisticated emulsions.

It is, therefore, an object of this invention to provide a means for obtaining a stable HIPE without the need for specialized emulsifiers.

It is a further object of this invention to provide a means for obtaining stable HIPE'S using conventional emulsifier compounds.

These and other objects of the instant invention are fulfilled in an improved high-internal-phase emulsion of the type comprising an aqueous phase, an oil phase, and an emulsifier; wherein the improvement comprises the inclusion of an amount sufficient to increase the stability of said emulsion of an electrolyte contained in said aqueous phase.

THE DISCLOSURE

Applicants have discovered that an improved high-internal-phase emulsion, i.e., having increased stability, can be obtained by the inclusion of an electrolyte in said emulsion. Specifically, the inclusion of an amount sufficient to increase the stability of said emulsion contained in the aqueous phase of a HIPE of the type comprising an aqueous phase, an oil phase, and an emulsifier will provide an increased stability of said emulsion especially when said emulsion is exposed to elevated temperature and freeze-thaw cycles.

The improved high-internal-phase emulsions of the instant invention include both water-in-oil and oil-in-water HIPE'S. That is, high-internal-phase emulsions having water or oil as the dispersed phase.

THE EMULSIFIER

The emulsifiers of the instant invention are conventional emulsifiers applicable for use in low and mid-internal-phase emulsions. Generally, these are nonionic materials. Generally, such emulsifiers have an HLB value of about 1 to about 7 and preferably from about 2 to about 6. Examples of typical emulsifiers subject to the instant invention include, but are in no way limited to:

| Type | Representative Trademarked Product |
|---|---|
| sorbitan trioleates | ARLACEL 85 (Atlas Chemical Industries) |
| mono-, di-, and triphosphoric esters of oleic acid | HOSTAPHAT KO3OON (Hoechsi) |
| polyoxyethylene sorbitol hexastearates | ATLAS G-1050 (Atlas Chemical Industries) |
| ethylene glycol fatty acid esters | EMCOL EL-5- (Witco Chemical Co.) |
| Iglycerol mono-180 stearates | IMWITOR 78OK (Witco Chemical Co.) |
| sorbitan monooleates | ARLACEL 80 (Atlas Chemical Industries) |
| polyoxyethylene (2) oleyl ethers | BRIJ92 (Atlas Chemical Industries) |
| ether of glycerol and fatty alcohols | CREMOPHOR WO/A |
| sorbitan isostearates | ARLACEL 987 (Atlas Chemical Industries) |
| esters of polyalcohols | EMULTEX WS (La Tessilchimica) |
| polyethoxylated (2) oleyl alcohols | SIMUSOL 92 (Produits Chimiques de la Montagne Noire) |
| synthetic primary alcohol ethylene oxide condensates | SYNPERONIC A2 (ICI) |
| mono and diglycerides of fat forming fatty acids | ATMOS 300 (ICI) |

The above listing is representative of the various conventional emulsifying agents subject to the instant invention and should in no way be considered limiting. In fact, any emulsifier whose ability to stabilize a HIPE is improved by the inclusion of an electrolyte in the aqueous phase of said emulsion is within the contemplated invention.

Generally, the emulsifier can be present in said emulsion at a level of about 5 to about 30 percent by weight of the external phase of the HIPE. Usually, however, said emulsifier will be present at a level of about 7 to about 30 percent and preferably from about 10 to about 20 percent. Based upon percent by weight of the total emulsion, the quantity of emulsifier in the HIPE is generally about 0.5 to about 5, usually, about 0.5 to about 4 percent by weight of said emulsion and preferably about 0.5 to about 0 percent by weight of said emulsion.

THE OIL

As stated, the invention particularly relates to HIPE'S wherein the liquid/liquid immiscible dispersed systems are water and oil, i.e., the HIPE having an aqueous phase and an oil phase. By oil is meant a material, solid or liquid, but preferably liquid at room temperature that broadly meets the following requirements:
1. is only sparingly soluble in water;
2. has a low surface tension; and
3. possesses a characteristic greasy feel to the touch.

Additionally, since application of the emulsion may ultimately involve a drug or cosmetic use, the oil should be cosmetically and pharmaceutically acceptable. Materials contemplated under, the instant invention include, for example, but are in no way limited to: straight, branched or cyclic parafine compounds; vegetable oils; esters of fatty acids or alcohols and silicon oils. Preferably the oil should be non-polar and should contain branch chain alkyl groups. Very desirable are highly branched chain mineral oils.

Examples of preferred oils include, but are in no way limited to such oils as:
 (a) $C_{10}$ to $C_{12}$ isoparafines such as ISOPAR L
 (b) Squalane such as COSBIOL
 (c) Branched chain parafin oil such as VASELINE OIL
 (d) Petrolatum such as VASELINE
 (e) Ethyl hexylpalmitate such as Wickenol 155
 (d) $C_{16}$ to $C_{18}$ fatty alcohol di-isooctanoate such as CETIOL SN
 (f) Mineral oil such as that manufactured by ESSO
 (g) Polyisobutene such as PARLEAM With respect to the quantity of oil in these emulsions, the actual amount of oil is less material than the quantity of the oil phase which phase comprises the oil, which are soluble in oil and any other additional components of the emulsion is generally less than about 24 to 25 percent by volume. Usually, the oil phase is present at a level of about 2 to about 24 percent by volume and preferably at a level of about 3 to about 20 percent by volume of said emulsion. On the other hand, in o/w HIPE'S the level of the oil phase in said emulsion will be generally greater than about 74 to 75 percent by volume of said emulsion. Thus, if the emulsion contains a level of oil phase between about 25 and about 74 percent by volume of the emulsion, the emulsion ceases to be of the high internal phase type and will not exhibit the special properties and characteristics attributable to HIPE'S.

THE AQUEOUS PHASE

The aqueous phase comprises water, the electrolyte, and any other components of the emulsion which are soluble in water. As with respect to the quantity of oil in the emulsion, the actual amount of water is less material than the quantity of the aqueous phase. With respect to w/o HIPE'S, the quantity of the aqueous phase present in the emulsion is generally greater than about 74 to 75 percent by volume. Usually, the aqueous phase is present at a level of about 76 to about 98 percent by volume and preferably at a level of about 80 to about 97 percent by volume of said emulsion. On the other hand, in o/w HIPE'S, the level of the aqueous phase in said emulsion is generally less than about 24 to 25 percent by volume. In such emulsions the aqueous phase will usually be present at a level of about 2 to about 24 percent by volume and preferably at a level of about 3 to about 20 percent by volume of said emulsion.

THE NON-EMULSION PHASE

As previously stated, the HIPE'S of the instant invention comprise an oil phase, an aqueous phase, an emulsifier, and an amount sufficient to increase the stability of said emulsion of an electrolyte contained in said aqueous phase. The two phases, i.e., the oil phase and the aqueous phase themselves comprise respectively oil and water and those other ingredients of the emulsion or emulsion product which are soluble in the respective phases. For example, since by definition the electrolytes of the instant invention must be water soluble, said electrolytes will be part of the aqueous phase. Thus, the aqueous phase will comprise water, said electrolyte and any other desired components which are soluble in the aqueous phase. These additional components will be set forth in detail in the section dealing with additives which will follow.

With respect to the emulsifier, the emulsifier may be present as a component of either the oil phase or the aqueous phase. Generally, the emulsifier will be soluble in the external phase of the particular emulsion, however, in some instances the emulsifier may be mutually soluble in both the external and internal phases. In such specific cases of mutual solubility, however, the relative solubility will favor the external phase and as such it can generally be expected that the greatest distribution of the emulsifier will be found in the external phase. Accordingly, for w/o HIPE'S the oil phase can generally be presumed to comprise the oil, the emulsifier and any other desired components which are soluble in the oil phase. Again as with the the aqueous phase, these additional components will be set forth in detail in the section dealing with additives which will follow.

While the oil and aqueous phase comprise those other components of the emulsion which are soluble in the respective phases, still other materials may be incorporated into the emulsion or emulsion product which ingredients are neither soluble in the oil nor oil phase. These materials will be referred to, hereafter, as components of the non-emulsion phase.

As stated previously, HIPE'S possess radically different properties from emulsions of the low-, or medium-internal phase ratio types. In addition to those properties previously discussed, HIPE'S have the ability to suspend insoluble particulate matter a superior to other known systems. Because of this ability, HIPE'S are adaptable and desirable for use in products where an insoluble solid particulate material is to be incorporated in a liquid or semiliquid form. Examples of such products, but in no way limited there, are such things as cosmetics such as lipstick and pancake makeup rocket fuel containing finely divided combustible solids; salad dressings containing suspended whole food particles and seasonings; dentifrices containing abrasive polishing agents; and solid transport mediums for piping finely divided solids such as coal ores, grains, and the like.

With respect to emulsions and emulsion products containing such non-emulsion phases, the proportions of ingredients contained in the emulsion are exclusive of components of the non-emulsion phase. Thus, while an emulsion product, eg., an abrasive containing dentifrice, may contain non-emulsion phase components, and while said product would appear as a homogenious mixture, the calculation of the percentages of ingredients in said emulsion and the percent volume of the respective phases would exclude for calculation purposes the presence of non-emulsion phase ingredients. Accordingly, an emulsion product containing non-emulsion phase ingredients, should be viewed as a HIPE in combination with a non-emulsion constituent, wherein said constituent is suspended by said emulsion.

THE ELECTROLYTE

The improved stability of the HIPE'S of the instant invention is the result of the incorporation into the aqueous phase of said emulsion an amount sufficient to increase the stability of said emulsion of an electrolyte. By increased stability is meant that the resulting emulsion will be less likely to break into the two distinct immiscible liquid phases under adverse storage conditions and for extended periods of time.

Much work with previously indicated "stable" HIPE'S have proven disappointing when those emulsions were subjected to test conditions approximating conditions that would be expected to be encountered by commercial products. Previously, stability at room temperature for 30 to 45 days was held to be an indication of HIPE stability. Unfortunately, these conditions are far too mild to approximate what a commercial product might be subjected to. When such products were subjected to harsher storage conditions, i.e., 1. accelerated room temperature aging via periodic centrifugation;
2. storage at 125° F.; and
3. freeze-thaw (0° to 70°) cyclic storage, most, if not all, showed signs of deterioration of the emulsion.

The improved stability that is the result of the instant invention results from the incorporation of an amount sufficient to increase the stability of said emulsion of an electrolyte in the aqueous phase of the emulsion.

The amount of electrolyte required to stabilize a particular emulsion varies with respect to the composition of the emulsion, its intended use, the degree of stability required, and the electrolyte being used. Unfortunately, applicants have not been able to devise a means for predicting electrolyte effect. Some general observation within, for example, classes of electrolytes can be made. However, a worker in the art will have to perform some simple experimentation with the particular system with which he is involved to optimize both electrolyte species and quantity thereof for his particular application. This experimentation is rather simple, and within the scope of someone with ordinary skill in the art.

While any amount of electrolyte sufficient to increase the stability of the HIPE will suffice, generally, a level of about 0.001 to about 10 percent by weight of said electrolyte should be present in said aqueous phase. More desirably, the level of said electrolyte should be about 0.01 to about 10 percent by weight of said aqueous phase. Preferably, said electrolyte should be present at a level of about 1 to about 6 percent and most preferably at a level of about 2 to about 4 percent by weight of said aqueous phase.

While any electrolyte, which incorporated in an amount sufficient to stabilize a HIPE, provides improved stability, is contemplated by the instant invention it has been generally found that the preferred electrolytes of the instant invention are selected from the group consisting of:

1. inorganic electrolytes;
2. organic electrolytes;
3. complex polyelectrolytes; and
4. mixtures thereof.

Generally, it has been found that inorganic electrolytes are preferable based upon their ability to stabilize various emulsions, however, it should be remembered that this is a generality and that simple experimentation should be performed to determine the best system for a specific need.

While any inorganic electrolyte, which when incorporated in an amount sufficient to stabilize a HIPE, provides improved stability, is contemplated by the instant invention it has generally been found that the preferred inorganic electrolytes of the instant invention include those selected from the group consisting of:

water soluble:
1. monovalent inorganic salts;
2. divalent inorganic salts;
3. trivalent inorganic salts; and
4. mixtures thereof.

With respect to the inorganic water soluble salts, it has been found that generally the trivalent salts are preferable to the divalent salts which in turn are preferable to the monovalent salts. It should be remembered, however, that some simple experimentation will be required to chose the optimum inorganic water soluble salt for a particular application.

Of the water soluble monovalent inorganic salts, preferred salts include: alkali metal halides, alkali metal sulfates, alkali metal carbonates, alkali metal phosphates, and mixtures thereof. Of even more particular preference are potassium chloride and sulfate as well as sodium chloride and sulfates and lithium chloride.

Of the water soluble divalent inorganic salts, preferred salts include: alkaline earth halides, alkaline earth sulfates, alkaline earth carbonates, alkaline earth phosphates, heavy metal halides, heavy metal sulfates, heavy metal carbonates, heavy metal phosphates, and mixtures thereof. Particularly preferred salts include: magnesium chloride, calcium chloride, and magnesium sulfate.

Of the water soluble trivalent inorganic salts, preferred salts include: heavy metal halides, heavy metal carbonates, heavy metal phosphates, and mixtures thereof. A particularly preferred salt is alumuminum chloride.

While any organic electrolyte that when incorporated in an amount sufficient to stabilize a HIPE, provides improved stability is contemplated by the instant invention it has generally been found that the preferred organic electrolytes of the instant invention include those selected from the group consisting of:

water soluble:
1. salts of carboxylic acids;
2. salts of amino acids;
3. salts of organic phosphoric acids;
4. salts of organic phosphonic acids;
5. quaternary ammonium halides;
6. quaternary ammonium acetates; and
7. mixtures thereof.

Of the water soluble salts of carboxylic acids, preferred salts include: alkali metal carboxylic acids, preferred salts include: alkali metal carboxylates, alkaline earth carboxylates, heavy metal carboxylates, ammonium carboxylates, substituted ammonium carboxylates, and mixtures thereof. With respect to alkali metal, ammonium, and substituted ammonium carboxylates, preferred carboxylates include: acetates, citrates, butyrates, lactates. Cyclic aromatic carboxylates such as: benzoates, cyclic aliphatic carboxylates, and mixtures thereof. With respect to alkaline earth carboxylates, preferred carboxylates include: acetates, lactates, glycolates, and mixtures thereof. With respect to heavy metal carboxylates, preferred carboxylates include acetates.

Of the water soluble salts of amino acids, preferred salts include: alkali metal salts of amino acids, alkaline earth salts of amino acids, heavy metal salts of amino acids, ammonium salts of amino acids, substituted salts of amino acids, and mixtures thereof. Preferred amino acids include: glutamic acid, aspartic acid, glycine, α-alanine, β-alanine, serine, arginine hydrochloride, histidine hydrochloride, lysine hydrochloride, and mixtures thereof. Preferred salts include: sodium glutamate, potassium glutamate, sodium aspartate, and mixtures thereof.

Of the water soluble salts of organic phosphoric and phosphonic acids, preferred salts include: alkali metal salts, alkaline earth salts, heavy metal salts, ammonium salts, substituted ammonium salts, and mixtures thereof.

Of the water soluble quaternary ammonium halides or acetates, preferred quaternaries are of the general formula:

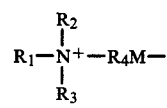

Wherein, $R_1$, and $R_2$, and $R_3$ are each selected from the group consisting of methyl, ethyl, isopropyl, hydroxymethyl, and hydroxyethyl, $R_4$ is an alkyl or alkenyl radical having 1 to about 22 carbon atoms; and M is a halide or acetate.

Of the water soluble salts of complex polyelectrolytes, preferred salts include: salts of polyacrylic acids, quaternary nitrogen substituted cellulose ethers, vinyl pyrrolidine/dimethyl amino ethyl methacrylate copolymers, salts of poly(methyl vinyl ether/mallic acid), alkyl substituted carboxy cellulosics, and mixtures thereof. Of the water soluble salts of polyacrylic acids, preferred salts include: polyacrylic acid, polyethyl acrylic acid, polymethyl acrylic acid, and mixtures thereof.

THE ADDITIVES

The emulsion, according to the instant invention, can be employed as a vehicle for a wide variety of products and uses. These include, but are in no way limited to such areas as summarized in Table 1. This listing is, of course, exemplary and by no means exhaustive; nor is the list of additives for any particular use exhaustive.

In particular, these improved HIPE'S are particularly attractive as vehicles for a wide variety of cosmetically or pharmaceutically active ingredients, particularly ingredients which have some beneficial effect when applied to the skin.

The emulsion thus provides a means whereby such active ingredients can be diluted, preserved, conveyed to and distributed on the skin surface at an appropriate concentration.

(A) MOISTURIZERS

A preferred use of HIPE'S is as a vehicle for a skin moisturizing product. Skin moisturizing actives as well as their appropriate required use levels are well known in the cosmetics art. These actives include, for example, but are in no way limited to such materials as:

1. sodium pyrollidone carboxylate
2. sodium lactate
3. lactic acid
4. triethanolamine lactate
5. orotic acid
6. inositol
7. sodium chloride
8. -hydroxy $C_6$ to $C_{10}$ carboxylic acids

TABLE 1

| | HIPE Emulsion Additives | | |
| | HIPE Composition | | |
| Application | Internal Phase | External Phase | Additives* |
| --- | --- | --- | --- |
| (i) FUELS | | | |
| Safety aircraft fuels | Aircraft fuel | Formamide, ethylene glycol & mixtures with water | |
| Jet and rocket fuel | Kerosene | Water | Finely divided combustible solid C, Al |
| Jet and rocket fuel | Kerosene | Hydrazine | Finely divided combustible solid C, Al |
| Fuel | Hydrocarbon fuel | Water | Corrosion inhibitors. Biocides Antifreeze etc. |
| Fuel | Hydrocarbon fuel | Glycols Dimethyl formamides Methanol | Combustible solids |
| Fuel | Hydrocarbon fuel | Polar liquid | Amido-ester stabilizers |
| Jet Fuel | Aircraft fuel | Formamide/urea Glycol/urea | Combustible solids |
| (ii) OIL FIELD APPLICATIONS | | | |
| Oil Well porosity reduction | Kerosene | Water | |
| Oil Well cleaning | Carbon disulphide | Water | |
| (iii) AGRICULTURAL | | | |
| Agricultural sprays | Water | Trimethylbenzene | Herbicides, insecticides |
| (iv) TEXTILE PROCESSING | | | |
| Textile printing pastes | Water | Hydrocarbon oil | Dyes |
| (v) FOODS | | | |
| Salad dressing | Water | Edible oil (corn oil etc.) | Flavorings, etc. |
| Creams | " | Edible oil (corn oil etc.) | Flavorings, etc. |
| (vi) HOUSEHOLD AND INDUSTRIAL CLEANING | | | |
| Hand cleaners | Water/glycerine | Kerosene/diglycol oleate | Perfume |
| Wax polish | Water | Kerosene/wax | |
| Silicone polish | Water | Silicone oil | |
| (vii) COSMETICS | | | |
| Insect repellent cream | Water | Mineral oil | Insect repellent |
| Sunscreen cream | Water | Mineral oil | UV screening agent |
| Antiperspirant cream | Water | Mineral oil | Aluminium chlorohydrate |
| Cosmetic cream | Water | Mineral oil | Sorbitol perfume antioxidant |
| Waterproof suntan cream | Water | Mineral oil/silicone oil | Sunscreen agent perfume |
| Hair cream | Water | Mineral oil | Sorbitol perfume |
| Acne cream | Water | Mineral oil | Benzoyl peroxide sulphur |
| Baby oil | Mineral oil/isopropyl | Water/ethanol | |

TABLE 1-continued

HIPE Emulsion Additives

| | HIPE Composition | | |
|---|---|---|---|
| Application | Internal Phase | External Phase | Additives* |
| | myristate | | |
| Tooth polish | Water | Mineral oil | Dicalcium phosphate |
| Bleaching cream | Water/hydrogen peroxide | Mineral oil | |
| (viii) MISC APPLICATIONS | | | |
| Pipe cleaning | Kerosene | Water | Mineral acids |
| Transporting solids through pipes etc. | Kerosene water | Water kerosene | Finely divided solids, eg coal, ores, grain |
| Transport of polymers eg water sol. polymers for flocculation etc., enabling rapid dispersion at place of application | Water | Kerosene | Polyacrylates polyacrylamides etc. |
| Crowd control. Crowds can be sprayed with thick sticky HIPE'S | Water | Kerosene | Dyes, odorous agents toxicants |
| Fire extinguishing. A thick blanket of HIPE can be applied to a fire with a similar action to foam | Water | Hydrocarbon oil | |

*Excluding emulsifying agent and electrolyte.

Accordingly, a preferred aspect of the instant invention is a skin moisturizing product comprising an improved high internal phase emulsion; of the type comprising an aqueous phase, an oil phase, and an emulsifier. The improvement comprises: an amount sufficient to increase the stability of said emulsion of an electrolyte contained in said aqueous phase; in combination with an amount sufficient to provide a moisturizing effect to the skin when said emulsion is contacted to said skin of a skin moisturizing agent. The moisturizing agents, contemplated by this preferred aspect of the invention, include all cosmetically and physiologically acceptable moisturizing agents known in the art as well as compounds that will be found to exhibit such properties. It should be noted that where such actives exhibit electrolytic activity, said active may serve a dual purpose as providing the active basis for the product as well as the basis for stabilizing the product.

(B) SUNSCREENS

Another preferred use of HIPE'S is as a vehicle for a sunscreen agent. Sunscreen agents and their use levels are well known in the cosmetics art. These agents provide a means of protecting both skin and hair from the harmful effects of solar radiation. Typical of these actives include, but are in no way limited to, such materials as:

1. p-amino benzoic acid
2. propoxylated (2)ethyl p-amino benzoate
3. 2-hydroxy-4-n-octoxybenzophenone
4. dipropylene glycol salicylate
5. 2,2',4,4'-tetrahydroxybenzophenone
6. 2-hydroxy-4-methoxy benzophone-5-sulphonic acid
7. ethylexyl-2-cyano-3,3-diphenyl acrylate Accordingly, a preferred aspect of the instant invention is a sunscreen product comprising an improved high-internal-phase emulsion; of the type comprising an aqueous phase, an oil phase, and an emulsifier. The improvement comprises: an amount sufficient to increase the stability of said emulsion of an electrolyte contained in said aqueous phase in combination with an amount sufficient to provide a sunscreening effect when said emulsion is contacted to the skin or hair of a sunscreen agent. The sunscreen agents contemplated by this preferred aspect of the invention include all known cosmetically and physiologically acceptable sunscreen agents known to the art as well as compounds that will be found to possess such activity. Again, it should be noted that where such actives exhibit sufficient electrolytic activity, said active may serve a dual function providing both the basis for product stability and activity.

(C) ANTIBACTERIAL AGENTS

Another preferred use of HIPE'S is as a vehicle for an antibacterial agent. Antibacterial agents including germicides, fungicides, and other such agents are well known in both the cosmetic and pharmaceutical arts; and their use levels are well understood. These agents provide an effective means of providing antibacterial action on body surfaces as well as other surfaces. Typical of these actives include, but are in no way limited to such materials as:

1. 2-bromo-2-nitro propan-1,3-diol
2. cetyl pyridinium chloride
3. 3,4,4'-trichlorocarbanilide
4. 2,4,4'-trichloro-2'-hydroxydiphenyl ether
5. benzalkonium chloride
6. para-hydroxy benzoic acid
7. dehydroacetic acid Accordingly, a preferred aspect of the instant invention is an antibacterial product comprising an improved high-internal-phase emulsion; of the type comprising: an aqueous phase, an oil phase, and an emulsifier, the improvement comprising an amount sufficient to increase the stability of said emulsion of an electrolyte contained in said aqueous phase; in combination with an amount sufficient to provide antibacterial activity of an antibacterial agent. The antibacterial agents contemplated by this preferred aspect of the invention include all known cosmetically and physiologically acceptable antibacterial agents known in the art as well as compounds that will be found to possess such activity. Again, it should be noted that were such actives possess sufficient electrolytic activity, said actives may provide a dual function in providing both the basis for product stability and activity.

(D) DEODORANTS

Another preferred use of HIPE'S is as a vehicle for deolorants. Deodorant agents and their use levels are well known in the cosmetic art.

These agents provide an effective means of providing odor supresssion and/or odor masking. Typical of these deodorants include, but are in no way limited to such materials as:

1. 2-ethyl-1,3-hexane diol
2. 2,4,4' trichloro-2'-hydroxydiphenyl ether
3. zinc oxide
4. zinc phenylsulfonate Accordingly, a preferred aspect of the instant invention is a deodorant product comprising an improved high-internal-phase emulsion; of the type comprising an aqueous phase, an oil phase and an emulsifier, the improvement comprising an amount sufficient to increase the stability of said emulsion of an electrolyte contained in said aqueous phase; in combination with an amount sufficient to provide a deodorant effect when said product is applied to the skin of a deodorant agent. The deodorant agents contemplated by this preferred aspect of the invention include all known cosmetically and physiologically acceptable antibacterial agents known in the art as well as compounds that will be found to possess such activity. Again, it should be noted that where such actives possess sufficient electrolyte activity, said actives may provide a dual function in providing both the basis for product stability and activity.

(E) ANTIPERSPIRANTS

Another preferred use of HIPE'S is as a vehicle for antiperspirant compositions. Antiperspirant agents are well known in the cosmetic art and the use levels of said agents are also well understood. These agents provide an effective means for perspiration reduction. Typical of these agents include, but are in no way limited to, such materials as:

1. aluminium chlorhydrate
2. aluminium chloride
3. sodium aluminium chlorhydroxy lactate complex
4. zirconyl chlorhydrate Accordingly, a preferred aspect of the instant invention is an antiperspirant product comprising an improved high internal phase emulsion of the type comprising an aqueous phase, an oil phase, and an emulsifier, the improvement comprising an amount sufficient to increase the stability of said emulsion of an electrolyte contained in said aqueous phase; in combination with an amount sufficient to provide a deodorant effect when said product is applied to the skin of an antiperspirant agent. The antiperspirant agent contemplated by this preferred aspect of the invention include all known cosmetically and physiologically acceptable antiperpsirant agents known in the art as well as compounds that will be found to possess such activity. Again, it should be noted that where such actives possess sufficient electrolyte activity, said actives may provide a dual function in providing the basis for product stability and activity.

(F) THERAPEUTIC AGENTS

Another preferred use of HIPE'S is a vehicle for theraputic compositions. Theraputic compositions of the instant invention are essentially intended for typical application to the body surfaces. Theraputic compositions can serve various functions and may contain antibiotics such as neomycin, tetracycline, penicillin, and other such agents; steroids, for example, cortisone and prednisolone; rubefacients such as mustard oil and methyl salicylate; antifungal agents such as undecylenic acid and antiparasitic agents such as gamma-benzene hexachloride as well as healing promoters such as magnesium or zinc sulphate. This list is by no means exhaustive and should serve only to point out the various types of theraputic agents that may be combined with the HIPE'S of the instant invention. Accordingly, a preferred aspect of the instant invention is an antiperspirant product comprising an improved high internal phase emulsion of the type comprising an aqueous phase, an oil phase and an emulsifier, the improvement comprising an amount sufficient to increase the stability of said emulsion of an electrolyte contained in said aqueous phase; in combination with an amount sufficient to provide a theraputic effect when said product is applied to the skin of a theraputic agent. The theraputic agents contemplated by this preferred aspect of the invention include well-known therapeutic agents as well as compounds that will be found to possess such activity. Again, where such actives possess sufficient electrolytic activity, said active may provide a dual function in providing both the basis for product efficiency and stability.

(G) PARTICULATE INGREDIENTS

As previously stated, HIPE'S have the ability to suspend particulate material. As such, another preferred aspect of the invention are compositions in which there are suspended particulate matter. Any solid particulate matter insoluble in either of the phases and that will be suspended by one of the improved HIPE'S are contemplated by the invention.

The examples of such products would be pancake makeups, lipsticks, abrasive cleaning products, as well as previously mentioned jet fuels and foods such as salad dressings that contain suspended bits of food matter, condiments, and seasonings. This list is by no means exhaustive and only points out the broad types of products for which this application can be made. Accordingly, a preferred aspect of the instant invention is antiperspirant product comprising an improved high-internal-phase emulsion of the type comprising an aqueous phase, an oil phase, and an emulsifier, the improvement comprising an amount sufficient to increase the stability of said emulsion of electrolyte contained in said aqueous phase; in combination with particulate ingredients. In particular, preferred particulate ingredients are selected from the group consisting of abrasives pigments, opacifiers, and mixtures thereof.

(H) CLEANSING AGENTS

Another preferred use of HIPE'S is a vehicle for cleaning compositions. Cleansing compositions of the instant invention are essentially intended for use on the skin. However, the application can include cleansing agents for hard surfaces. Cleansing agents provide an effective means for removing dirt and grease from either of these surfaces. Typical of cleansing agents are, but in no way limited to, such materials as: soaps, anionic, nonionic, cationic, zwitterionic, surfaces active agents, and mixtures thereof. These agents are well known in the detergent and cosmetic art and their use levels for various applications are also well understood.

Accordingly, preferred aspect of the instant invention is a cleansing product comprising an improved high-internal-phase emulsion of the type comprising an aqueous phase, an oil phase, and an emulsifier. The improvement comprises an amount sufficient to increase the stability of said emulsion of an electrolyte contained in said aqueous phase in combination with an amount sufficient to provide a cleansing effect of a cleansing agent. The cleansing agents contemplated by this preferred aspect of the invention include all non-cleansing agents that are cosmetically and physiologically acceptable and that are also compatible with said HIPE emulsion. Additionally, contemplated within the scope of the invention are those compounds that will be found to exhibit similar properties. Again, where such actives possess sufficient electrolytic activity, said actives may provide a dual function in providing both the basis for a product activity and stability.

(I) POLYMERIC MATERIALS

An additional preferred use of HIPE'S, in particular water-in-oil HIPE'S, is as a vehicle for water soluble polymeric materials. Water soluble polymeric materials are used in the cosmetic arts for facial masks and hair sprays. These materials, presented in a aqueous medium such as water-in-oil high-internal-phase emulsion, can be applied to the skin or hair; and upon the evaporation of the water, forms a stiff film or coating on those surfaces. These agents are well known in the cosmetic art and the use levels of said agents are well understood. These polymeric materials provide an effective means of holding hair set as well as the removal of unwanted contaminants on the skin via a facial mask.

Accordingly, preferred aspect of the instant invention is a high-internal-phase emulsion of the type comprising an aqueous phase, an oil phase, and an emulsifier. The improvement comprising an amount sufficient to increase the stability of said emulsion of electrolyte contained in said aqueous phase in combination with water soluble polymeric material as selected from the group consisting of facial mask polymeric materials and hair spray polymeric materials. The polymeric materials contemplated by this preferred aspect of the invention include all non-cosmetically and physiologically acceptable polymeric agents known in this art as well as those compounds that will be found to possess such activity.

(J) COSMETIC ADJUNCT MATERIALS

Still another preferred use of HIPE's is a vehicle for cosmetic ingredients that will be applied to the skin. By cosmetic adjunct ingredient is meant materials which either perfume or color the skin. Perfumes and colorants are well known in the cosmetic art and have been incorporated in emulsions of low and medium internal-phase ratios. The use levels in emulsions are also well understood.

Accordingly, preferred aspect of the instant invention is antiperspirant product comprising an improved high-internal-phase emulsion as set forth above in combination with ingredients selected from the group consisting of perfume and coloring agents.

Additional materials, as well as combinations of the above materials in a single product, are contemplated within the scope of the invention. These additional materials include such functional adjuncts as antioxidants, such as, but in no way limited to: tocopherol, ascorbyl palmitate, propyl gallate, butylated hydroxy toluene, butylated hydroxyanisole, and mixtures thereof; propellants, such as, but in no way limited to: trichlorofluoro methane, dichlorodifluoro methane, dichlorotetrafluoro ethane, monochlorodifluoro methane, trichlorotrifluoro ethane, propane, butane, isobutane, dimethyl ether, carbon dioxide, and mixtures thereof; solvents, such as, but in no way limited to: ethyl alcohol, 2-ethylhexanol, ethylene carbonate, propylene carbonate, methylene chloride, isopropyl alcohol, castor oil, linear ethoxylated polymer of methanol, ethylene glycol monoethyl ether, diethylene glycol monobutyl ether, diethylene glycol monoethyl ether, propoxylated butanol, propoxylated oleyl alcohol, butyl stearate, butyl myristate, and mixtures thereof; humectants, such as, but in no way limited to: glycerin, sorbitol, sodium 2-pyrollidone-5-carboxylate, soluble collagen, dibutyl phthalate, gelatin, polyglycerogen, ethoxylated (10–20 moles) glucose, propoxylated (10–20 moles) glucose, and mixtures thereof; thickiners for the oily phase, such as, but in no way limited to: tetra alkyl and/or trialkyl aryl ammonium smectites, chemically modified magnesium aluminium silicate, organically modified montmorillonite clay, fumed silica, hydroxyethyl stearate amide, and mixtures thereof; emollients, such as, but in no way limited to: stearyl alcohol, glyceryl monoricinoleate, glyceryl monostearate, sulphated tallow, propylene glycol, mink oil, cetyl alcohol, stearyl stearate, isopropyl isostearate, dimethyl brassylate, stearic acid, isobutyl palmitate, isocetyl stearate oleyl alcohol, myristyl stearate, isopropyl lanolate, isopropyl laurate, hexyl laurate, decyl oleate, di-isopropyl adipate, 2-octadecanol, iso-cetyl alcohol, myristyl ethoxymyristate, cetyl palmitate, dimethylpolysiloxane, di-n-butyl sebacate, di-isopropyl sebacate, di-2-ethyl hexyl sebacate, 2-ethyl hexyl palmitate isononyl isononanoate, isodecyl isononanoate, isotridecyl isononanoate, 2-ethyl hexyl palmitate, 2-ethyl hexyl stearate, di-(2-ethyl hexyl)adipate, di-(2-ethyl hexyl)succinate, isopropyl myristate, isopropyl palmitate, isopropyl stearate, butyl stearate, glyceryl monostearate, polyethylene glycols, propylene glycol, triethylene glycol, lanolin, castor oil, acetylated lanolin alcohols, acetylated lanolin, petrolatum, isopropyl ester of lanolin fatty acids, mineral oils, butyl myristate, isostearic acid, palmitic acid, isopropyl linoleate, cetyl lactate, laury lactate, myristyl lactate, quaternised hydroxy alkyl aminogluconate, decyl oleate, isodecyl oleate, di-isopropyl adipate, 2-ethyl hexyl palmitate, isostearyl neopentanoate, myristyl myristate, di-isopropyl adipate, oleyl ethoxy myristate, di-glycol stearate, ethylene glycol monostearate, and mixtures thereof.

PREPARATION OF THE EMULSION

The emulsions and emulsion products of the instant invention may be prepared via a batch or continuous process. In fact, any processing techniques already available to the HIPE art, may be employed with the singular modification of the step of adding an electrolyte to the aqueous phase of said emulsion.

With respect to batch processing, the emulsifier is dissolved or dispersed in the oil to form the basic oil phase; and the electrolyte is added to the water to form the basic aqueous phase. The oil phase is then transferred to a mixing vessel and the aqueous phase is continuously added thereto in small aliquots under constant mixing.

For the purposes of viscosity control, it has been found desirable to first prepare a rather coarse and fluid emulsion of the desired composition by slow mixing during the incorporation of the aqueous phase. Once the desired amount of aqueous phase has been incorporated, the speed of mixing is increased and the period extended until the desired consistency of the emulsion is obtained.

In instances where the emulsion contains ingredients that will be part of either the aqueous or oil phases, these ingredients should be incorporated into the basic phases prior to bringing the phases together. In instances where the emulsion will have ingredients in a non-emulsion phases, these ingredients may be dispersed in one of the two phases prior to making the emulsion; or they may be blended and mixed into the emulsion once it is formed.

STABILITY OF THE EMULSIONS

As stated previously, previous assessments of stability, i.e. 30 to 45 days standing at room temperature, are insufficiently rigorous to evaluate products intended for commercial use. Because of this, several accelerated tests were designed to subject the emulsions of the instant invention to greater strain. These tests are as follows:

(A) ACCELERATED ROOM TEMPERATURE AGING VIA PERIODIC CENTRIFUGATION

To study stability towards repeated centrifugation, a known portion of emulsion or emulsion product is placed in a graduated centrifuge tube and centrifuged periodically (i.e. every 2 to 5 days) at 2,000 r.p.m. for 5 minutes. The volume of aqueous phase which separated was then recorded.

(B) HIGH TEMPERATURE STABILITY

High temperature stability is assessed by storing sealed samples of the emulsion or emulsion product at 125° F. These samples are then examined for phase separation with respect to length of storage.

(C) ROOM TEMPERATURE STABILITY

Room temperature stability is accomplished in the same manner as the high temperature stability with the exception that samples are stored at 70° F.

(D) FREEZE-THAW STABILITY

To assess freeze-thaw stability, sealed samples of emulsion or emulsion product are subjected to cycled temperatures between about 0° F. and 70° F. One such cycle, i.e. 0° F. to 70° F. to 0° F., being about 48 hours. At the end of the cycles, samples are examined for phase separation.

EXAMPLES

The following examples will illustrate further the present invention without, however, limiting the same thereto. All percentages in the examples will follow the conventions previously set forth unless otherwise indicated. In particular, all electrolyte levels are based on the aqueous phase.

Several abbreviations will be used during the examples, the such abbreviations are generally trade mark names for chemical compounds. The following is a listing of the names of emulsifiers and identification of their chemical composition and manufacturer.

| Emulsifier | Composition | Supplier |
|---|---|---|
| Igepal Ca 420 | Ethoxylated octyl phenol | GAF |
| Brij 92 | Ethoxylated (2) oleyl ether | ICI |
| Span 80 | Sorbitan monooleate | ICI |
| Span 85 | Sorbitan trioleate | ICI |
| Atmos 300 | Mono and di glycerides of fat forming fatty acids | ICI ICI |
| Drewmulse GMO | Glycerol monooleate | PVO |
| Kessco Ester | Glycerol monooleate | ARMAK |
| Drewpole 10-4-0 | Decaglycerol tetraoleate | PVO |
| Liposorb SQO | Sorbitan Sesquioleate | Lipo Chemicals |
| Magnesium oleate Volpo 3 | Ethoxylated (3) oleyl ether | Croda Chemicals |
| Hodag GMR | Glycerol mono ricinoleate | Hodag |

EXAMPLE 1

Stability of Several Water-in-Oil HIPE'S (91% Internal Phase) Towards Periodic Centrifugation at Room Temperature Several water-in-oil HIPE'S were prepared using mineral oil or kerosene as the oil component of the oil phase. The emulsions were prepared by dissolving or dispersing the emulsifier in the oil phase and dissolving the electrolyte, if any, in the water of the aqueous phase. The aqueous phase was then added in the aliquots to the oil phase under constant mixing. Samples of the resulting emulsions were then transferred to centrifuge tubes to be stored at room temperature. Periodically (i.e. every 2 to 5 days) the samples were centrifuged at about 2,000 r.p.m. for about 5 minutes. Percent separation of the aqueous phase was recorded with respect to time. The results of this experiment are shown in Table 2. The table system refers to the emulsifier oil mixture.

It is clear from Table 2 that the emulsifying ability of all the quite different emulsifiers tested (ranging in HLB from 1.8–6.6) is greatly enhanced by electrolyte. It appears from Table 2, that divalent salts, such as $K_2SO_4$ and $M_gSO_4$, are more effective than monovalent salts such as KCl or KSCN. It is also seen in Table 2 that the relative stabilizing effect of the salts depends on the particular emulsifier used.

The room temperature shelf stability of these emulsions paralleled the behavior recorded in Table 2. In some cases, the effect of electrolyte was even more dramatic. For example, water-in-mineral oil HIPE's prepared from glycerol monooleate (PVO) coarsened badly after 1 month and broke after ca. 2 months. Identical emulsions containing 0.5 molar $MgSO_4$ or 0.5 molar $K_2SO_4$ showed no change in appearance or texture and showed no water separation after 10 months!

EXAMPLE 2

Influence of Electrolyte on High Temperature (125° F.) Stability of Water-in-Mineral Oil HIPE'S Several water-in-oil HIPE'S were prepared similarly as in Example 1. The HIPE'S were then subjected to storage at 125° F. for up to 200 days. Phase separation as percent water separated was recorded versus time. The results of this experiment are given in Table 3. The phase ratio of these emulsions was 91 percent aqueous phase. Again, the enhanced stability in the presence of electrolyte is evident regardless of the HLB of the emulsifier (2.8-6.0). It is clear from Table 3 that certain electrolytes such as MgSO₄, sodium polyacrylate, and sodium lactate are capable of greatly increasing the high temperature stabilizing ability of the emulsifiers. Certain electrolytes such as AlCl₃ and LiCl were not particularly effective in enhancing high temperature stability. However, it will be shown that these electrolytes were quite effective in increasing freeze-thaw stability.

EXAMPLE 3

Influence of Electrolyte on Freeze-Thaw Stability of Several Water-in-Oil HIPE'S Several water-in-oil HIPE'S were prepared similarly as in Examples 1 and 2. These HIPE'S were then subjected to 48 hour freeze-thaw cycles (i.e. one cycle is

TABLE 2

Stability of Several Water-In-Oil HIPE'S (91% Aqueous Phase) Towards Periodic centrifugation at Room Temperature

| System[a] | Electrolyte | Time (days) | % Separation of Aqueous Phase | Condition[b] |
|---|---|---|---|---|
| Drewmulse GMO - M.O. | Distilled water | 110 | 14 | VL,G |
| Drewmulse GMO - M.O. | 0.1 molar KCl | " | 0 | S,W |
| Drewmulse GMO - M.O. | 0.1 molar K₂SO₄ | " | 0 | VS,W |
| Span 85 - M.O. | Distilled water | 60 | 62.5 | VL,G |
| Span 85 - M.O. | 0.1 molar KCl | " | 21.6 | S,W |
| Span 85 - M.O. | 0.1 molar KSCN | " | 33.3 | L,W |
| Kessco GMO - M.O. | Distilled water | 14 | 100 | — |
| Kessco GMO - M.O. | 1% sodium polyacrylate | 55 | 0 | S,W |
| Kessco GMO - M.O. | 1% Polymer JR | 53 | 0 | S,W |
| Kessco GMO - M.O. | 0.5% K₂SO₄ | 56 | 1.0 | S,W |
| Kessco GMO - M.O. | 0.5% MgCl₂ | 55 | 0 | S,W |
| Kessco GMO - M.O. | 0.1% MgCl₂ | 55 | 1.3 | S,W |
| Volpo 3 - M.O. | Distilled water | 15 | 4.0 | VL,G |
| Volpo 3 - M.O. | 0.001 molar AlCl₃ | 60 | 0 | S,W |
| Span 80 - M.O. | Distilled water | 108 | 12.2 | VL,W |
| Span 80 - M.O. | 0.1 molar KCl | " | 0 | S,W |
| Span 80 - M.O. | 0.1 molar K₂SO₄ | " | 0 | VS,W |
| Igepal Ca 420 - M.O.* | Distilled water | 80 | 59.8 | VL,G |
| Igepal Ca 420 - M.O.* | 0.1 molar KCl | " | 11.6 | L,W |
| Igepal Ca 420 - M.O.* | 0.1 molar K₂SO₄ | " | 0.5 | S,W |
| Igepal Ca 420 - kerosene | Distilled water | 51 | 100 | — |
| Igepal Ca 420 - kerosene | 0.1 molar KCl | " | 38.7 | L,G |
| Igepal Ca 420 - kerosene | 0.1 molar K₂SO₄ | " | 0 | S,W |
| Igepal Ca 420 - kerosene | 0.1 molar MgCl₂ | " | 0.6 | S,W |
| Brij 92 - M.O. | Distilled water | 107 | 1.5 | L,W |
| Brij 92 - M.O. | 0.1 molar KCl | " | 1.5 | L,W |
| Brij 92 - M.O. | 0.1 molar K₂SO₄ | " | 0.7 | VL,G |
| Span 85 - M.O. | Distilled water | 90 | 74 | VL,G |
| Span 85 - M.O. | 0.1 molar KCl | " | 18 | S,W |
| Span 85 - M.O. | 0.1 molar K₂SO₄ | " | 19 | VS,W |

[a]The concentration of emulsifier is 10% by volume based on the volume of the oil phase except those indicated as * which are 20%. M.O. is Carnation mineral oil (Witco Chemicals). The emulsifiers are identified in Table 1.
[b]VL = Very Loose; L = Loose; S = Stiff; VS = Very Stiff; W = White; and G = Gray.

TABLE 3

Examples of the Influence of Electrolyte on the High Temperature (125° F.) Stability of Water-in-Mineral Oil[a] HIPE'S

| Emulsifier | Electrolyte | Time of Storage (days) | % Separation of water |
|---|---|---|---|
| Atmos 300 | Distilled water | 49 | 100 |
| " | 1% MgCl₂ | " | 0 |
| " | 1% K₂SO₄ | " | 0 |
| " | 6% Sodium lactate[b] | " | 0 |
| " | 1% Sodium polyacrylate | " | 0 |
| " | 1% CaCl₂ | " | 0 |
| " | 1% MgSO₄ | " | 0 |
| " | " | 115 | 0 |
| " | 4% CaCl₂ | " | 80 |
| " | 1% Sodium polyacrylate | " | 0 |
| " | 4% K₂SO₄ | " | 0 |
| " | 1% K₂SO₄ | " | 100 |
| " | 1% LiCl | 49 | 100 |
| " | 1% AlCl₃ | " | 100 |
| Drewpol 10-4-0 | Distilled water | 49 | 100 |
| " | 6% Sodium lactate[b] | " | 10 |
| " | 4% Sodium polyacrylate | " | 0 |
| " | 4% MgSO₄ | " | 0 |
| " | 4% AlCl₃ | " | 0 |
| " | 4% Sodium polyacrylate | 200 | 0 |
| " | 4% MgSO₄ | " | 0 |

[a]The mineral oil was Marcol 52 (Exxon). All emulsions were 91% aqueous phase by volume. The emulsifier concentration was 20% by volume based on the volume of the oil phase.
[b]The sodium lactate was actually a buffer system of lactic acid and sodium lactate at pH ~ 6.

70° F. to 0° F. to 70° F.). Percent seperation of water was recorded versus time.

The influence of electrolyte on the freeze-thaw stability of several water-in-mineral oil (Marcol-52, Exxon) HIPE'S (91% aqueous phase by volume) is recorded in Table 4. Here again, the influence of electrolyte is quite dramatic. In fact, all emulsions prepared with the emulsifiers listed in Table 1 broke down completely after one freeze-thaw cycle in the absence of the electrolyte. With certain electrolytes such as LiCl, $AlCl_3$, $MgSO_4$ or sodium polyacrylate, over 100 cycles could be tolerated without deterioration of the emulsions. It should be noted that the concentrations of electrolyte used in all the freeze-thaw experiments were much less than that required to supress the freezing point of the aqueous phase below 0° F. Thus, the influence of electrolyte on freeze-thaw stability is not produced by lowering of the freezing point.

EXAMPLE 4

Influence of Electrolyte on the Freeze-Thaw Stability of Complex Water-in-Oil HIPE'S Example 3 was repeated, this time employing complex mixtures of materials in the oil phase. The stability results are shown in Table 5. Table 5 shows that electrolytes are capable of improving the stability of such complex emulsions.

TABLE 4

Influence of Electrolyte on the Freeze-Thaw Stability of Several Water-in-Mineral Oil HIPE'S[a]

| Emulsifier | Electrolyte | Time of Storage (days) | % Separation of water |
|---|---|---|---|
| Atmos 300 | Distilled water | 2 | 100 |
| " | 1% $MgCl_2$ | 49 | 0 |
| " | 1% $AlCl_2$ | " | 0 |
| " | 1% $K_2SO_4$ | " | 0 |
| " | 6% Sodium lactate[b] | " | 0 |
| " | 1% Sodium polyacrylate | " | 0 |
| " | 1% $CaCl_2$ | " | 10 |
| " | 1% $MgSO_4$ | " | 0 |
| " | 1% LiCl | " | 0 |
| " | 4% $AlCl_3$ | 115 | 0 |
| " | 1% $K_2SO_4$ | " | 0 |
| " | 4% $MgSO_4$ | " | 0 |
| " | 4% LiCl | " | 0 |
| " | 4% LiCl | 200 | 0 |
| Drewpol 10-4-0 | Distilled water | 2 | 100 |
| " | 4% Sodium polyacrylate | 49 | 0 |
| " | 4% $MgSO_4$ | " | 0 |
| " | 4% $AlCl_3$ | " | 0 |
| " | 6% Sodium lactate[b] | " | 0 |
| " | 4% $MgCl_2$ | " | 0 |
| " | 6% Sodium lactate | 115 | 0 |
| " | 4% $MgSO_4$ | " | 0 |
| " | 4% $AlCl_3$ | " | 0 |
| Volpo 3 | Distilled water | 2 | 100 |
| " | 4% $MgSO_4$ | 49 | 0 |
| " | 4% Sodium polyacrylate | " | 40 |
| " | 4% $MgSO_4$ | 115 | 0 |
| " | 4% $AlCl_3$ | " | 0 |

[a]The mineral oil used was Marcol-52 (Exxon). All emulsions were of 91% by volume aqueous phase. The emulsifier concentration was 20% by volume based on the volume of the oil phase.
[b]The sodium lactate was actually a buffer solution of lactic acid and sodium lactate at pH = 6.

TABLE 5

Influence of Electrolyte on the Freeze-Thaw Stability Of Water-in-Oil HIPE'S[a]

| Composition of Oil Phase[b] | Electrolyte | Time of Storage (days) | % Separation of water |
|---|---|---|---|
| Atmos 300-20% Isopropyl Palmitate-10% Marcol-52-70% | Distilled water | 2 | 100 |
| Atmos 300-20% Isopropyl Palmitate-10% Marcol-52-70% | 4% LiCl | 49 | 0 |
| Atmos 300-20% Isopropyl Palmitate-10% Marcol-52-70% | 4% $MgCl_2$ | " | 0 |
| Atmos 300-20% Isopropyl Palmitate-10% Marcol-52-70% | 4% $MgSO_2$ | " | 0 |
| Atmos 300-20% Isopropyl Palmitate-10% Marcol-52-70% | 4% $AlCl_3$ | " | 0 |
| Atmos 300-20% Isopropyl Palmitate-10% Marcol-52-70% | 4% $K_2SO_4$ | " | 0 |
| Atmos 300-20% Isopropyl Palmitate-10% Marcol-52-70% | 6% Sodium lactate[c] | " | 0 |

TABLE 5-continued

Influence of Electrolyte on the Freeze-Thaw Stability Of Water-in-Oil HIPE'S[a]

| Composition of Oil Phase[b] | Electrolyte | Time of Storage (days) | % Separation of water |
|---|---|---|---|
| Atmos 300-20% Isopropyl Palmitate-10% Marcol-52-70% | 4% LiCl | 115 | 0 |
| Atmos 300-20% Isopropyl Palmitate-10% Marcol-52-70% | 4% $MgCl_2$ | " | 0 |
| Atmos 300-20% Isopropyl Palmitate-10% Marcol-52-70% | 4% $MgSO_4$ | " | 0 |
| Atmos 300-20% Isopropyl Palmitate-10% Marcol-52-70% | 4% $AlCl_3$ | " | 0 |
| Atmos 300-20% Isopropyl Palmitate-10% Marcol-52-70% | 6% Sodium lactate[c] | " | 0 |
| Atmos 300-20% Isopropyl Palmitate-10% Marcol-52-70% | 4% $K_2SO_4$ | " | 0 |
| Atmos 300-20% Safflower oil-10% Isopropyl palmitate-10% Hydrophobic silica-2% Klearol Mineral Oil-58% | Distilled water | 2 | 100 |
| Atmos 300-20% Safflower oil-10% Isopropyl palmitate-10% Hydrophobic silica-2% Klearol Mineral Oil-58% | 6% Sodium lactate | 49 | 0 |
| Atmos 300-20% Safflower oil-10% Isopropyl palmitate-10% Hydrophobic silica-2% Klearol Mineral Oil-58% | 4% $K_2SO_4$ | " | 0 |
| Atmos-300-20% Safflower oil-40% Marcol-52-40% | Distilled water | 2 | 100 |
| Atmos-300-20% Safflower oil-40% Marcol-52-40% | 4% $CaCl_2$ | 115 | 0 |
| Atmos 300-20% Safflower oil-10% Marcol-52-70% | Distilled water | 2 | 100 |
| Atmos 300-20% Safflower oil-10% Marcol-52-70% | 4% $K_2SO_4$ | 49 | 0 |
| | 4% LiCl | " | 0 |
| | 4% $AlCl_3$ | " | 0 |
| Atmos 300-20% Safflower oil-10% Marcol-52-70% | 4% $MgSO_4$ | " | 0 |
| Atmos 300-20% Safflower oil-10% Marcol-52-70% | 4% Sodium polyacrylate | " | 0 |
| Atmos 300-20% Safflower oil-10% Marcol-52-70% | 6% Sodium lactate | " | 0 |
| Atmos 300-20% Safflower oil-10% Marcol-52-70% | 4% $CaCl_2$ | " | 0 |
| Atmos 300-20% Safflower oil-10% Marcol-52-70% | 4% $MgCl_2$ | " | 0 |
| Atmos 300-20% Safflower oil-10% Marcol-52-70% | 4% $K_2SO_4$ | 115 | 0 |
| Atmos 300-20% Safflower oil-10% Marcol-52-70% | 4% $MgSO_4$ | " | 0 |
| Atmos 300-20% Safflower oil-10% Marcol-52-70% | 4% Sodium polyacrylate | " | 0 |
| Atmos 300-20% Safflower oil-10% Marcol-52-70% | 6% Sodium lactate[c] | " | 0 |
| Atmos 300-20% Hydrophobic silica-2% Marcol-52-78% | Distilled Water | 2 | 100 |
| Atmos 300-20% Hydrophobic silica-2% Marcol-52-78% | 4% $CaCl_2$ | 49 | 0 |

TABLE 5-continued

Influence of Electrolyte on the Freeze-Thaw Stability Of Water-in-Oil HIPE'S[a]

| Composition of Oil Phase[b] | Electrolyte | Time of Storage (days) | % Separation of water |
|---|---|---|---|
| Atmos 300-20% Hydrophobic silica-2% Marcol-52-78% | 4% MgCl$_2$ | " | 0 |
| Atmos 300-20% Hydrophobic silica-2% Marcol-52-78% | 6% Sodium lactate | " | 0 |
| Atoms 300-20% Hydrophobic silica-2% Marcol-52-78% | 4% K$_2$SO$_4$ | " | 0 |
| Atmos 300-20% Hydrophobic silica-2% Marcol-52-78% | 4% MgSO$_4$ | " | 0 |
| Atmos 300-20% Hydrophobic silica-2% Marcol-52-78% | 4% AlCl$_3$ | " | 0 |
| Atmos 300-20% Hydrophobic silica-2% Marcol-52-78% | 4% LiCl | " | 0 |
| Atmos 300-20% Hydrophobic silica-2% Marcol-52-78% | 4% K$_2$SO$_4$ | 115 | 0 |
| Atmos 300-20% Hydrophobic silica-2% Marcol-52-78% | 4% MgSO$_4$ | " | 0 |
| Atmos 300-20% Hydrophobic silica-2% Marcol-52-78% | 4% AlCl$_3$ | " | 0 |
| Atmos 300-20% Hydrophobic silica-2% Marcol-52-78% | 4% MgSO$_4$ | 200 | 0 |
| Atmos 300-20% Hydrophobic silica-2% Marcol-52-78% | 4% Sodium polyacrylate | " | 0 |

[a]All emulsions were 91% aqueous phase by volume.
[b]Composition is by volume based on the oil phase except for hydrophobic silica which is by weight of oil phase. All emulsions contained methyl and propyl paraben as preservatives.
[c]The sodium lactate was actually a buffer solution of sodium lactate-lactic acid at pH = 6.

EXAMPLE 5

Water-in-Oil HIPE'S

The following HIPE'S were prepared in a similar manner as in the previous examples. The oil employed was mineral oil, and the emulsifier was Span 80. The emulsifier was present at a level of about 10 percent of the oil phase. In each case the HIPE'S containing electrolyte exhibited very much superior stability to those without electrolytes.

| INTERNAL PHASE VOLUME | ELECTROLYTE |
|---|---|
| 95% by volume | 1% KCl |
| 95% by volume | 1% K$_2$SO$_4$ |
| 95% by volume | none |
| 97% by volume | 1% KCl |
| 97% by volume | 1% K$_2$SO$_4$ |
| 97% by volume | none |

EXAMPLE 6

Oil-in-Water Emulsion

The following HIPE'S were prepared using the oil phase as the internal phase. Mineral oil was employed with an equal part mixture of Span 80, Tween 80, and Tween 20 as the emulsifier. The emulsifier was present at a level of 10 percent by volume of the oil phase. The oil phase comprised 91 percent by volume of the emulsion. HIPE'S containing electrolytes were more stable than those without electrolytes.

| INTERNAL PHASE (91%) | ELECTROLYTE |
|---|---|
| Mineral oil; and | 0.01 M KCl |
| 10% mixture of Span 80, Tween 80 and Tween 20, | 1.0 M CaCl$_2$ |
| 10% mixture of Span 80, Tween 80 and Tween 20, 80 | none |
| | 1.0 M CaCl$_2$ |
| | none |

EXAMPLE 7

An oil-in-water HIPE, according to Example 6, was made this time by employing 4 to 6M CaCl$_2$ as the electrolyte. The resulting emulsions were virtually transparent.

EXAMPLES 8 AND 9

These examples illustrate emulsions according to the invention in the form of gels for topical application to the skin as moisturizing products.

| | Components Percent by Weight | |
|---|---|---|
| | 8 | 9 |
| HOSTAPHAT KO300N | 3 | — |
| IMWITOR 78OK | — | 3 |
| ISOPAR L | 15 | 15 |
| Sodium glutamate | 2.5 | 2.5 |
| Triethanolamine lactate - 50%: pH 5.5 (moisturizing agent) | 6 | 6 |
| Para P[(1)] | 0.1 | 0.1 |
| 1, 3-butylene glycol | 3 | 3 |

| | Components Percent by Weight | |
|---|---|---|
| | 8 | 9 |
| Water | 70.4 | 70.4 |

(1) propyl p-hydroxybnezoate

The oil was mixed with the emulsifier, the Para P added and dissolved at a temperature of 60°–70° C. The aqueous phase containing the amino acid, the lactate and the glycol were heated gently at 45°–50° C. Finally, the emulsion was prepared after cooling by emulsifying the aqueous phase with the oily phase to provide a water-in-oil emulsion at a temperature no higher than 50° C.

EXAMPLES 10-12

Emulsions having the following formulation as further examples of skin moisturizing products for topical application, were prepared by the method described for Examples 8 and 9.

| Ingredients | Example 10 (cream) | Example 11 (cream) | Example 12 (lotion) |
|---|---|---|---|
| HOSTAPHAT KO3OON | 2.5 | — | 3 |
| IMWITOR 78OK | — | 2.5 | — |
| ISOPAR L | 7.5 | 5 | 7.5 |
| Mineral oil (ESSO) | — | 5 | — |
| Parleam(1) | — | — | 7.5 |
| Para P | 0.1 | 0.1 | 0.1 |
| Triethanolamine lactate (50%), pH 5.5 | 6 | 6 | 6 |
| 1-3 butylene glycol | 3 | 3 | 3 |
| Sodium glutamate | 2.5 | 2.5 | 2.5 |
| Water | 78.4 | 75.9 | 70.4 |

(1) hydrogenated polyisobutene
O oily phase
A aqueous phase

EXAMPLE 13

This example illustrates the formulation of a cream for topical application to the skin:

| | % w/w |
|---|---|
| CREMOPHOR W O/A | 3 |
| Mineral oil (ESSO) | 13 |
| Glycine | 3 |
| Triethanolamine lactate (pH 5.5) | 3 |
| 1, 3-butylene glycol | 3 |
| Para M(1) | 0.2 |
| Para P | 0.1 |
| Perfume | 0.2 |
| Water | 74.5 |

(1) methyl p-hydroxybenzoate

EXAMPLE 14

This example also illustrates the formulation of a cream for topical application to the skin:

| | % w/w |
|---|---|
| CREMOPHOR W O/A | 2.5 |
| LYTOL(i) | 8.65 |
| MODULAN(ii) | 1 |
| CEREWAX L | 0.25 |
| Triethanolamine lactate (pH 5.5) | 6 |
| Sodium glutamate | 2.5 |
| 1, 3-butylene glycol | 3 |
| Para P | 0.1 |

| | % w/w |
|---|---|
| Water | 76 |

(i) Light branched chain polycyclic mineral oil supplied by WITCO CHEMICALS
(ii) Acetylated lanolin supplied by AMERCHOL

EXAMPLE 15

This example illustrates the formulation of a lotion for topical application to the skin:

| | % w/w |
|---|---|
| ARLACEL 987 | 3.5 |
| ISOPAR L | 7 |
| Parleam | 8 |
| Sodium pyrollidone carboxylate (50% solution) | 4 |
| 1, 3-butylene glycol | 3 |
| Sodium glutamate | 3 |
| Para p | 0.1 |
| Para M | 0.2 |
| Perfume | 0.2 |
| Water | 71 |

EXAMPLE 16

This example also illustrates the formulation of a lotion for topical application to the skin:

| | % w/w |
|---|---|
| Parleam | 8 |
| Mineral oil (ESSO) | 8 |
| BRIJ 92 | 3 |
| 1, 3-butylene glycol | 3 |
| Collagen hydrolysate | 3 |
| Zinc sulphate | 0.5 |
| Para P | 0.1 |
| Para M | 0.2 |
| Perfume | 0.2 |
| Water | 74 |

EXAMPLE 17

This example also illustrates the formulation of a cream for topical application to the skin:

| | % w/w |
|---|---|
| HOSTAPHAT KO3OON | 3 |
| Parleam | 5 |
| Mineral oil (ESSO) | 5 |
| 1, 3-butylene glycol | 3 |
| Collgen hydrolysate | 3 |
| Sodium chloride | 3 |
| Para P | 0.1 |

-continued

|  | % w/w |
|---|---|
| Para M | 0.2 |
| Perfume | 0.2 |
| Water | 77.5 |

EXAMPLES 18–29

In the following Examples the various commercial application of HIPE'S are illustrated.

| | EXAMPLES | | | | | |
|---|---|---|---|---|---|---|
| | 18 | 19 | 20 | 21 | 22 | 23 |
| % Aqueous Phase | 91% | 89% | 90% | 92% | 91% | 92% |
| Oil | Mineral | Corn | Mineral | Mineral | Corn | Mineral |
| Emulsifier | Drewpol 10-4-0 | Drewpol 10-4-0 | Atmos 300 | Atmos 300 | Drewpol 10-4-0 | Drewpol 10-4-0 |
| Electrolyte | 4% $K_2SO_4$ | 4% $MgSO_4$ | 1% $MgSO_4$ | 4% $K_2SO_4$ | 4% NA polyacrylate | 4% $MgSO_4$ |
| Adjunct | 1% sodium pyrollidone carboxylate | 1% sodium pyrollidone carboxylate | 3% aluminum chlorohydrate | 3% aluminum chlorohydrate | 5% para amino benzoic acid | 3% triethanol amino stearate |
| Use | Moisturizer | Moisturizer | Antiperspirant | Antiperspirant | Sunscreen | Cleansing Lotion |

| | EXAMPLES | | | | | |
|---|---|---|---|---|---|---|
| | 24 | 25 | 26 | 27 | 28 | 29 |
| % Aqueous Phase | 5% | 89% | 91% | 92% | 91% | 89% |
| Oil | Petrolatum | Mineral | Mineral | Mineral | Mineral | Mineral |
| Emulsifier | Span 80 | Atmos 300 | Atmos 300 | Atmos 300 | Drewpol 10-4-0 | Drewpol 10-4-0 |
| Electrolyte | 1% $CaCl_2$ | 4% $MgSO_4$ | 4% $MgSO_4$ | 4% $ZnSO_4$ | 4% $MgSO_4$ | 4% $ZnSO_4$ |
| Adjunct | 20% by weight of emulsion of crushed mother of pearl | 3% 2-ethyl-1 3-hexane diol | 1% cetyl pyridinium chloride | neomycin | 3% coco butter 5% para-amino benzoic acid 1% sodium pyrollidone carboxylate | 1.5% dehydroxy acetone 5% para-amino benzoic acid 3% coco butter |
| Use | Lip gloss or Eye liner | Deodorant | Antibacterial cream | Antibacterial cream | Sunscreen with moisturizer | Suntan promoter |

We claim:

1. An improved high-internal-phase emulsion of the type comprising an aqueous phase, an oil phase and an emulsifier, the improvement comprising:
   an amount sufficient to increase the stability of said emulsion of an electrolyte selected from the group consisting of potassium sulfate and magnesium sulfate contained in said aqueous phase
   thereby providing for increased stability of said emulsion.

2. An improved high-internal-phase emulsion according to claim 1, wherein the internal phase of said emulsion is said aqueous phase.

3. An improved high-internal-phase emulsion according to claim 2, wherein said emulsifier is present at a level of about 5 to about 30 percent by weight of the external phase of said emulsion.

4. An improved high-internal-phase emulsion according to claim 2, wherein said electrolyte is present at a level of about 0.001 to about 10 percent by weight of said aqueous phase.

5. An improved high-internal-phase emulsion according to claim 2, further comprising an amount sufficient to provide a moisturizing effect to the skin when said emulsion is contacted to said skin of a skin moisturizer.

6. An improved high-internal-phase emulsion according to claim 2, further comprising an amount sufficient to provide a sunscreening effect when said emulsion is contacted to the skin or hair, of a sunscreen agent.

7. An improved high-internal-phase emulsion according to claim 2, further comprising an amount sufficient to provide antibacterial activity of an antibacterial agent.

8. An improved high-internal-phase emulsion according to claim 2, further comprising an amount sufficient to provide deodorant activity when said emulsion is applied to the skin of a deodorant.

9. An improved high-internal-phase emulsion according to claim 2, further comprising an amount sufficient to provide antiperspirant active material.

10. An improved high-internal-phase emulsion according to claim 2, further comprising an amount sufficient to provide a therapeutic effect of a therapeutic agent.

11. An improved high-internal-phase emulsion according to claim 2, further comprising solid particulate matter suspended in said emulsion.

12. An improved high-internal-phase emulsion according to claim 11, wherein said solid particulate matter is selected from the group consisting of:
    (i) abrasives;
    (ii) pigments
    (iii) opasifiers; and
    (iv) mixtures thereof.

13. An improved high-internal-phase emulsion according to claim 2, further comprising a cleansing agent selected from the group consisting of:
    (i) anionic surface active agents;
    (ii) nonanionic surface active agents;
    (iii) cationic surface active agents;
    (iv) zwitterionic surface active agents;
    (v) soap; and
    (vi) mixtures thereof.

14. An improved high-internal-phase emulsion according to claim 2, further comprising water soluble polymeric materials.

15. An improved high-internal-phase emulsion according to claim 14, wherein said water soluble polymeric material is selected from the group consisting of:

(i) facial mask polymeric materials; and
(ii) hair spray polymeric materials.

16. An improved high-internal-phase emulsion according to claim 2, further comprising at least one ingredient selected from the group consisting of:
(i) perfume; and
(ii) coloring agents.

17. An improved high-internal-phase emulsion according to claim 3, wherein said emulsifier is present at a level of about 7 to about 30 percent by weight of the external phase of said emulsion.

18. An improved high-internal-phase emulsion according to claim 17, wherein said emulsifier is present at a level of about 10 to about 20 percent by weight of the external phase of said emulsion.

19. An improved high-internal-phase emulsion according to claim 4, wherein said electrolyte is present at a level of about 0.01 to about 10 percent by weight of said aqueous phase.

20. An improved high-internal-phase emulsion according to claim 19, wherein said electrolyte is present at a level of about 1 to about 6 percent by weight of said aqueous phase.

21. An improved high-internal-phase emulsion according to claim 20 wherein said electrolyte is present at a level of about 2 to about 4 percent by weight of said aqueous phase.

22. An improved high-internal-phase emulsion according to claim 1, wherein the internal phase of said emulsion is said oil phase.

23. An improved high-internal-phase emulsion according to claim 22, wherein said emulsifier is present at a level of about 5 to about 30 percent by weight of the external phase of said emulsion.

24. An improved high-internal-phase emulsion according to claim 23, wherein said emulsifier is present at a level of about 7 to about 30 percent by weight of the external phase of said emulsion.

25. An improved high-internal-phase emulsion according to claim 24, wherein said emulsifier is present at a level of about 10 to about 20 percent by weight of the external phase of said emulsion.

26. An improved high-internal-phase emulsion according to claim 23, wherein said electrolyte is present at a level of about 0.001 to about 10 percent by weight of said aqueous phase.

27. An improved high-internal-phase emulsion according to claim 26, wherein said electrolyte is present at a level of about 0.01 to about 10 percent by weight of said aqueous phase.

28. An improved high-internal-phase emulsion according to claim 27, wherein said electrolyte is present at a level of about 1 to about 6 percent by weight of said aqueous phase.

29. An improved high-internal-phase emulsion according to claim 28, wherein said electrolyte is present at a level of about 2 to 4 percent by weight of said aqueous phase.

30. An improved high-internal-phase emulsion according to claim 22, further comprising an amount sufficient to provide a moisturizing effect to the skin when said emulsion is contacted to said skin, of a skin moisturizer.

31. An improved high-internal-phase emulsion according to claim 22, further comprising an amount sufficient to provide a sunscreening effect when said emulsion is contacted to the skin or hair, of a sunscreen agent.

32. An improved high-internal-phase emulsion according to claim 22, further comprising an amount sufficient to provide antibacterial activity of an antibacterial agent.

33. An improved high-internal-phase emulsion according to claim 22, further comprising an amount sufficient to provide deodorant activity when said emulsion is applied to the skin of a deodorant.

34. An improved high-internal-phase emulsion according to claim 22, further comprising an amount sufficient to provide antiperspirant activity when said emulsion is applied to the skin of an antiperspirant active material.

35. An improved high-internal-phase emulsion according to claim 22, further comprising an amount sufficient to provide a therapeutic effect of a therapeutic agent.

36. An improved high-internal-phase emulsion according to claim 22, further comprising solid particulate matter suspended in said emulsion.

37. An improved high-internal-phase emulsion according to claim 36, wherein said particulate matter is selected from the group consisting of:
(i) abrasives;
(ii) pigments
(iii) opasifiers; and
(iv) mixtures thereof.

38. An improved high-internal-phase emulsion according to claim 22, further comprising a cleansing agent selected from the group consisting of:
(i) anionic surface active agents;
(ii) nonanionic surface active agents;
(iii) cationic surface active agents;
(iv) zwitterionic surface active agents;
(v) soap; and
(vi) mixtures thereof.

39. An improved high-internal phase emulsion according to claim 22, further comprising at least one ingredient selected from the group consisting of:
(i) perfume; and
(ii) coloring agents.

40. An improved process for preparing a high-internal-phase emulsion of the type comprising an aqueous phase, an oil phase and an emulsifier and prepared by the steps comprising:
(i) dissolving said emulsifier in oil to provide said oil phase; and
(ii) homogenizing said oil phase with said aqueous phase to provide said high-internal-phase emulsion, the improvement comprising:
(i) dissolving an amount sufficient to increase the stability of said emulsion of an electrolyte selected from the group consisting of potassium sulfate and magnesium sulfate contained in said aqueous phase thereby providing for increased stability of said emulsion.

41. An improved process according to claim 40, wherein the internal phase of said emulsion is said aqueous phase.

42. An improved process according to claim 41, wherein:
(i) said emulsifier is present at a level of about 30 percent by weight of the external phase of said emulsion; and
(ii) said electrolyte is present at a level of about 0.001 to about 10 percent by weight of said aqueous phase.

43. An improved process according to claim 40, wherein:

(i) the internal phase of said emulsion is said oil phase;

(ii) said emulsifier is present at a level of about 5 to about 30 percent by weight of external phase of said emulsion; and (iii) said electrolyte is present at a level of about 0.001 to about 10 percent by weight of said aqueous phase.

* * * * *